US00PP35157P2

(12) United States Plant Patent
Carmi et al.

(10) Patent No.: US PP35,157 P2
(45) Date of Patent: May 9, 2023

(54) MANDARIN TREE NAMED 'MA'AYANA'

(50) Latin Name: *Citrus reticulata*
Varietal Denomination: Ma'ayana

(71) Applicant: The State of Israel, Ministry of Agriculture and Rural Development, Agricultural Research Organization (ARO) (Volcani Institute), Rishon Lezion (IL)

(72) Inventors: Nir Carmi, Rechovot (IL); Yosef Yaniv, Rehovot (IL); Kanonich Yeoshua, Yavne (IL)

(73) Assignee: The State of Israel, Ministry of Agriculture and Rural Development, Agricultural Research Organization (ARO) (Volcani Institute), Rishon Lezion (IL)

( * ) Notice: Subject to any disclaimer, the term of this patent is extended or adjusted under 35 U.S.C. 154(b) by 27 days.

(21) Appl. No.: 17/803,249

(22) Filed: Mar. 31, 2022

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202
CPC ..... A01H 6/785; A01H 5/08
See application file for complete search history.

*Primary Examiner* — Keith O. Robinson
(74) *Attorney, Agent, or Firm* — Michelle Bos Legal LLC

(57) ABSTRACT

"Ma'ayana' mandarin tree produces seedless, easy-peeling flavorful fruit that ripens mid-season.

4 Drawing Sheets

Latin name: *Citrus reticulata.*
Common Name: Mandarin.
Variety denomination: 'Ma'ayana'.

BACKGROUND AND SUMMARY OF THE VARIETY

'Ma'ayana' is a new mandarin tree that originated from a controlled cross of female parent 'Idit' (not patented) with male parent 'Nova' (not patented) at Rishon Lezion, Israel in 1993. A seedling produced from the cross was irradiated in 1998, and was subsequently selected for propagation by grafting onto rootstock at Rishon Lezion in 2005. The resulting tree, given the name 'Ma'ayana', was observed to produce seedless, easy-peeling flavorful fruit that ripens mid-season. 'Ma'ayana' mandarin tree has been observed to remain true to type over successive asexually propagated generations.

BRIEF DESCRIPTION OF THE PHOTOGRAPHS

The accompanying photographs, which show 'Ma'ayana' mandarin grown on 'Troyer' strange rootstock (not patented), were taken in 2021 and 2022 at Rishon Lezion, Israel. The trees were planted in 2016. The colors of the claimed variety may vary with lighting conditions. Therefore, color characteristics of the variety should be determined with reference to the observations described herein, rather than from these illustrations alone.

Figure 1:
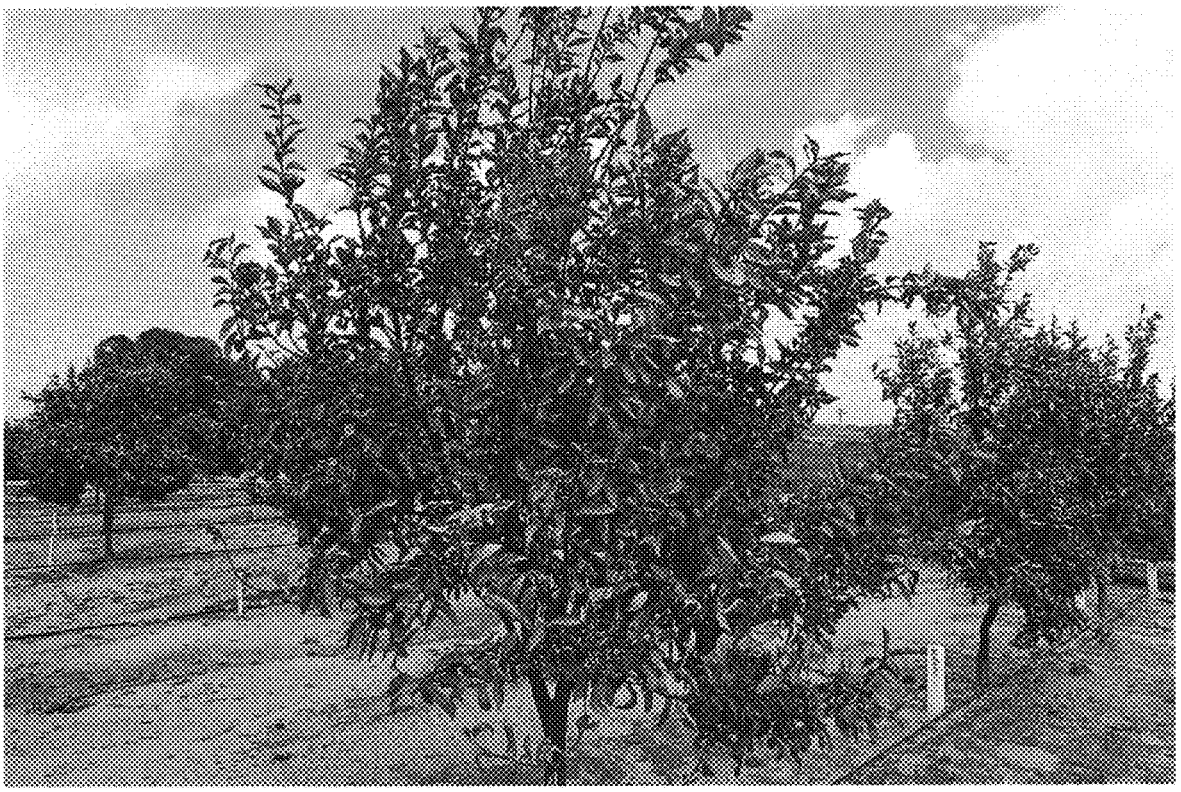
Figure 2:
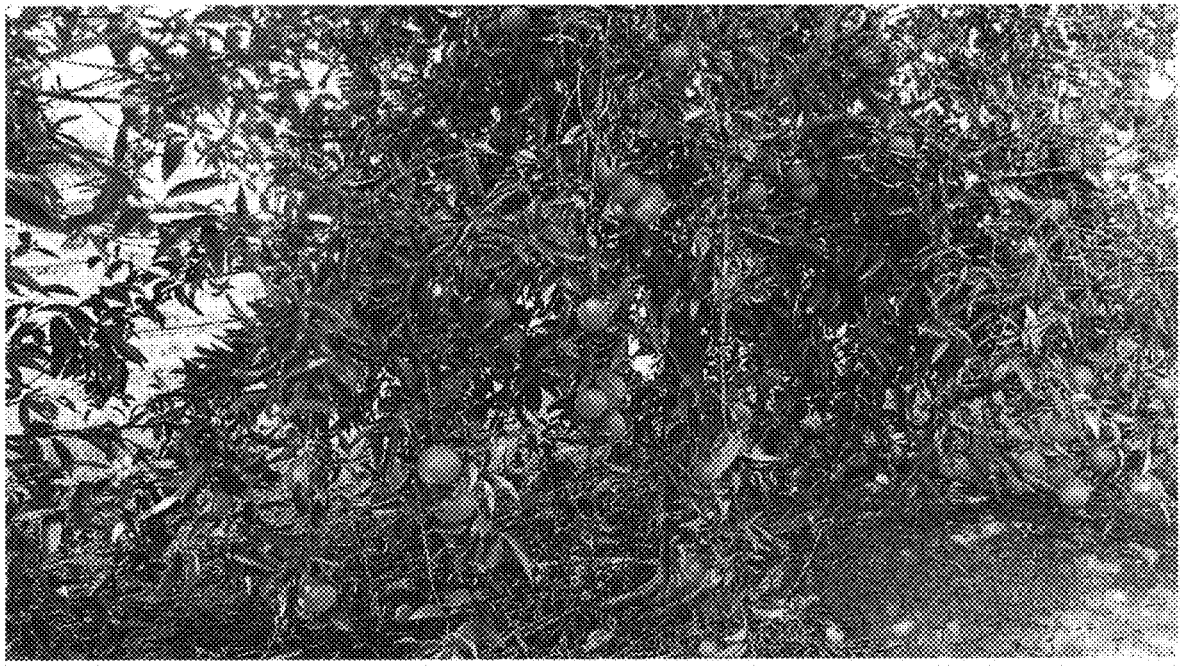
Figure 3:
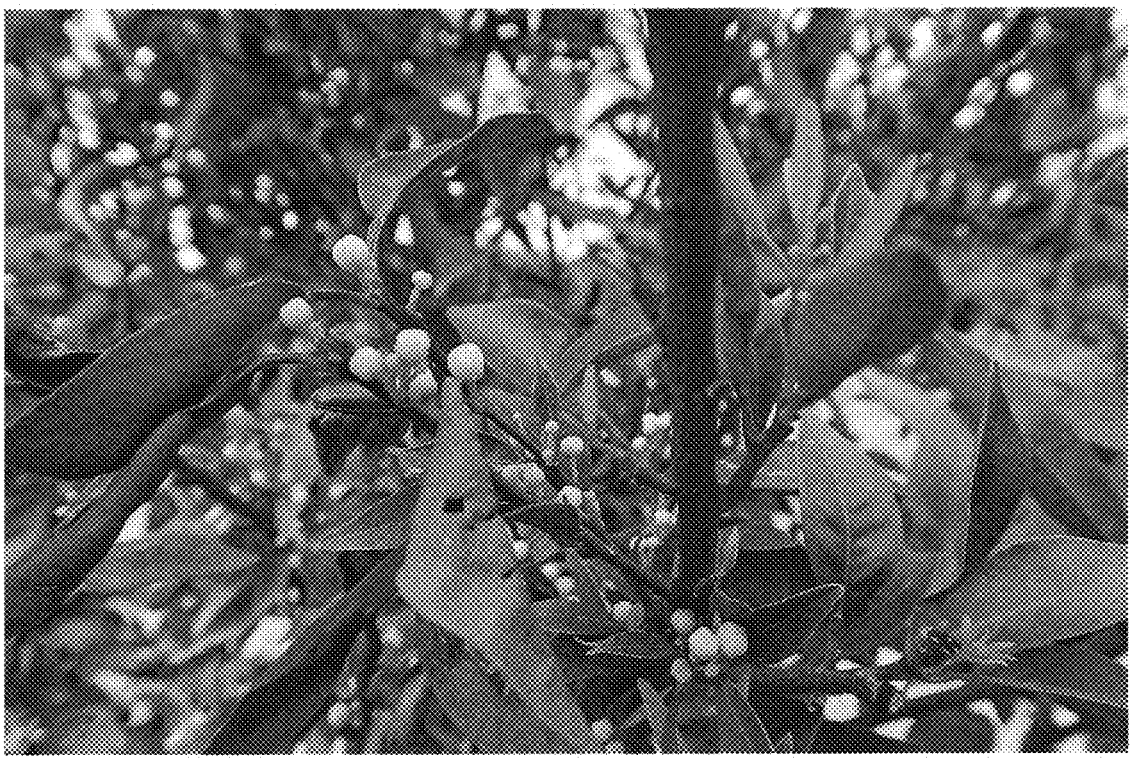
Figure 4:
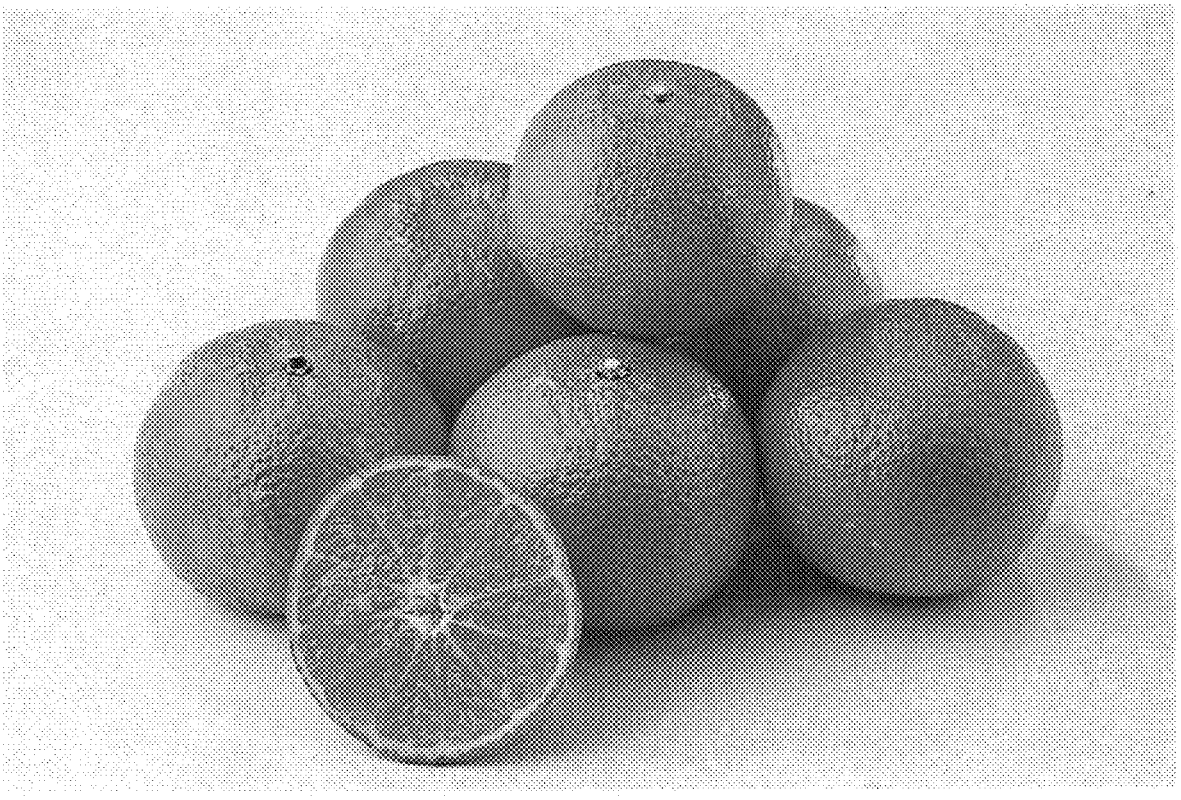

FIG. 1 shows a 'Ma'ayana' mandarin tree;
FIG. 2 shows a 'Ma'ayana' mandarin tree and fruit;
FIG. 3 shows buds and blossoms on a 'Ma'ayana' mandarin tree; and
FIG. 4 shows whole and sectioned 'Ma'ayana' mandarins.

DETAILED BOTANICAL DESCRIPTION

The following detailed botanical description is based on observations recorded at Rishon Lezion, Israel in 2021 and 2022. The trees described were planted in 2016 on 'Troyer' citrange rootstock. The characteristics described will vary somewhat depending upon cultural practices, climatic conditions, location and growing season. Quantified measurements are expressed as an average of measurements taken from a number of individual plants of the claimed variety. The measurements of any individual plant or any group of plants of the variety may vary from the stated average. Colors are described with reference to The RHS Colour Chart, $2^{nd}$ edition (Royal Horticultural Society 1986).

DETAILED BOTANICAL DESCRIPTION

Tree:
- *Vigor.*—Medium strong.
- *Density of canopy.*—Medium dense.
- *Habit.*—Spreading.
- *Height.*—2.5 m to 3 m.
- *Trunk diameter* (*at* 30 *cm above the graft*).—16 cm to 20 cm.
- *Bark texture.*—Rough.
- *Bark color.*—Brown 200B with greyed-orange 169B overcolor.

Branch (fruiting branches about 1 m above graft):
- *Length.*—About 2 m.
- *Diameter.*—6 cm to 7 cm.
- *Crotch angle.*—Semi-upright.
- *Bark color.*—Brown 200B with greyed-orange 169B overcolor.
- *Bark texture.*—Slightly rough.
- *Thorns.*—Few.

Flowers:
- *Bud shape.*—Globose.
- *Bud length.*—4 mm to 5 mm.
- *Bud diameter.*—4 mm to 5 mm.
- *Bud color.*—Yellow-green 150A.

*Quantity of blossoms per cluster.*—Varies, usually 1 to 5.
*Blossom diameter.*—25 mm to 28 mm.
*Blossom depth.*—11 mm to 14 mm.
*Sepal length.*—1 mm.
*Sepal width.*—2 mm.
*Sepal shape.*—Triangular.
*Sepal color-lower surface.*—Yellow-green 145C.
*Quantity of petals per flower.*—5.
*Petal shape.*—Lanceolate.
*Petal apex.*—Obtuse.
*Petal margin.*—Entire.
*Petal length.*—14 mm to 15 mm.
*Petal width.*—4 mm to 6 mm.
*Petal color-upper surface.*—White 155B.
*Petal color-lower surface.*—White 155B.
*Pedicel length.*—4 mm to 6 mm.
*Pedicel diameter.*—1 mm.
*Pedicel color.*—Yellow-green 144B.
*Pistil quantity per flower.*—1.
*Stigma color .*—Greyed-yellow 162A.
*Style length.*—5 mm.
*Style color.*—Yellow-green 145A.
*Anther quantity per flower.*—About 20.
*Stamen length.*—6 mm to 7 mm.
*Anther color.*—Greyed-orange 163B.

Leaves:
*Length.*—70 mm to 90 mm.
*Width.*—30 mm to 40 mm.
*Length/width ratio.*—1.75 to 3.0.
*Blade margin.*—Entire with few incisions; some undulation present.
*Leaf shape.*—Broadly elliptic; some blistering present.
*Apex shape.*—Obtuse to slightly acute; emarginate tip.
*Base shape.*—Rounded.
*Texture of upper surface.*—Smooth with prominent central vein.
*Color of upper surface.*—Dark green 146A.
*Color of lower surface.*—Medium green 146C.
*Petiole length.*—7 mm to 11 mm.
*Petiole color-upper surface.*—Yellow-green 146A.
*Petiole color-lower surface.*—Yellow-green 146C.
*Wings.*—Present.
*Wing width.*—Less than 1 mm.

Fruit:
*Axial diameter.*—65 mm to 79 mm.
*Apical diameter.*—48 mm to 60 mm.
*Weight.*—110 g to 130 g.
*General shape in profile.*—Slightly obloid.
*Shape in cross-section.*—Round.
*Position of maximum diameter.*—Equator.
*Neck.*—Absent.
*Navel.*—Absent.
*Areola.*—Absent.
*Depression at distal end.*—Small, shallow.
*Rind color.*—Vivid reddish orange N34B.
*Oil gland diameter.*—Small, about 1 mm.
*Rind thickness.*—3 mm.
*Ease of peeling.*—Easy.
*Rind texture.*—Smooth.
*Rind glossiness.*—Medium.
*Albedo color.*—Pale yellow 158A.
*Adherence of albedo to flesh.*—Medium.
*Filling of core.*—Half-filled.
*Diameter of core relative to fruit.*—Small.
*Quantity of fruit segments per fruit.*—9 to 11.
*Toughness of segment membrane.*—Weak.
*Juice sac length.*—Short, 8 mm to 10 mm.
*Juice sac shape.*—Elongated, thin.
*Juice sac color.*—Strong orange N25A.
*Fruit flesh color.*—Strong orange N25A.
*Juice soluble solids.*—14° Brix.
*Relative harvest maturity.*—Early to medium.
*Seeds.*—None or very few.
*Parthenocarpy.*—Present.
*Pest and disease resistance.*—None noted.
*Pest and disease susceptibility.*—None noted.

We claim:

1. A new and distinct mandarin tree named 'Ma'ayana' substantially as described and illustrated herein.

* * * * *